United States Patent [19]

Aeschlimann et al.

[11] 4,236,666

[45] Dec. 2, 1980

[54] LABORATORY CENTRIFUGE

[75] Inventors: Hans-Peter Aeschlimann, Neckarsteinach; Volker Schmidhuber, Bammental; Werner Kappes, Eberbach, all of Fed. Rep. of Germany

[73] Assignee: Dr. Molter GmbH, Bammental, Fed. Rep. of Germany

[21] Appl. No.: 20,184

[22] Filed: Mar. 13, 1979

[30] Foreign Application Priority Data

Mar. 13, 1978 [DE] Fed. Rep. of Germany ....... 2810765

[51] Int. Cl.$^3$ ........................ B04B 9/12; G01N 33/48

[52] U.S. Cl. ........................................ 233/26; 422/72

[58] Field of Search ........................ 422/72, 73; 233/26

[56] References Cited

U.S. PATENT DOCUMENTS

| | | | |
|---|---|---|---|
| 3,905,772 | 9/1975 | Hartnett et al. | 233/26 X |
| 3,935,995 | 2/1976 | Williams et al. | 233/26 |
| 3,951,334 | 4/1976 | Fleming et al. | 233/26 |
| 4,092,113 | 5/1978 | Hardy | 422/72 |

*Primary Examiner*—R. E. Serwin

*Attorney, Agent, or Firm*—Daniel M. Rosen

[57] ABSTRACT

A laboratory centrifuge for producing suspensions, sediments and the like, and for carrying out washing and similar processes, in which a motor-driven vertical shaft is arranged in a housing, said shaft carrying a shaft head on which magazines or such are pivotably mounted for receiving sample containers. The shaft head can be driven in either of two opposing directions and has two brackets arranged symmetrically to the axis of rotation the outwards extending arms of said brackets carrying an axle on which the magazines are pivotably mounted with axial play. The width of the magazines is slighter than the distance between the two bracket arms, and a locking device is present between the bracket arms and the magazines, becoming effective when the magazine abuts the respective bracket arm.

11 Claims, 5 Drawing Figures

LABORATORY CENTRIFUGE

BACKGROUND OF THE INVENTION

The present invention relates to a laboratory centrifuge for producing suspensions, sediments and the like, the carrying out of washing-and similar processes, in which a motor-driven vertical shaft is arranged in a housing, said shaft carrying a shaft head on which magazines or such are pivotably mounted for receiving sample containers.

Laboratory centrifuges are already known which have the aforementioned structure. With some of these centrifuges it is known to lock the sample container-receiving magazines in a certain inclined position using magnets for example, so as to remove the liquid from the sample containers during the subsequent centrifugal action. The expense required for this is quite considerable. The magazines are furthermore only held in the desired position through the magnetic forces, which would lead to operational defect if the magnetic field failed. These defects would be extremely disturbing, especially with automatic running of the operation program. As long as the magazine container on the shaft head are mechanically lockable by hand, and interruption of the operating process will be necessary, and this prevents a fully automatic run of the process.

SUMMARY OF THE INVENTION

The invention is based on the task of improving a laboratory centrifuge of the type in question so that the magazines containing the sample containers automatically and securely take up the position desired during their fast or less fast rotation about the centrifugal axis in order to avoid operation defects caused through the magazines not taking up the intended position.

It is also a task of the invention, to construct the members for obtaining this purpose in a manner that is as simple as possible and still is fail-safe.

For solving this task, the invention suggests forming the laboratory centrifuge in question in such a way that the shaft head which can be driven in either of two opposite directions of rotation, has two brackets arranged symmetrically to the axis of rotation, facing each other. The outward extending arms carry an axle in the area of their outer ends, on or with which the magazines for the sample containers are pivotably mounted with axial play. The width of the magazine is slighter than the distance between both bracket arms, and there is a locking device between the bracket arms and the magazines, becoming effective when the magazine abuts the respective bracket arm.

Further features of this improved laboratory centrifuge according to the invention are shown through the sub-claims and the following description of a particularly preferred embodiment of the invention which is schematically shown in the FIGS. 1 to 5 of the drawings and which is subsequently described in greater detail.

DESCRIPTION OF THE DRAWINGS

Figure 1:
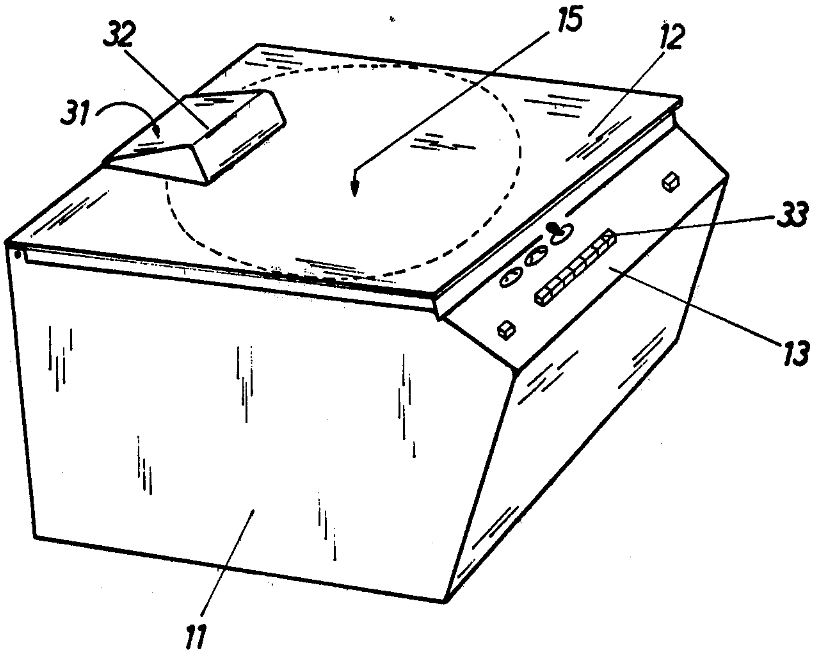
FIG. 1 shows a perspective outside view of the laboratory centrifuge

In the housing 11 with latch-type cover 12 and control panel 13 arranged on the front side, the drive motor for the centrifuge is situated in the lower area and sets the shaft 14 with shaft head 15 in rotation. The shaft can be driven in counter clockwise or clockwise direction. Brackets 17 and 18 are arranged on opposing sides on the shaft head 15, relative to the axis of rotation 16, with outwards extending arms **19*a*, 19*b* which carry the magazines 20 whose bores 21 take up the sample containers 22. The magazines 20 are mounted on the outer ends of the bracket arms 19*a*, 19*b* via the axle 23 which has both its ends hung in the slots 24 in the bracket arms 19*a*, 19*b*. The width of the magazines 20 is considerably slighter than the distance between the bracket arms 19*a*, 19*b* of the two brackets 17 and 18, so that when the magazines 20 abut the bracket arm 19*a* with their one lateral surface 25, there is a play S present between the opposing lateral surface 26 of the magazine and the neighboring bracket arm 19*b*. This play is greater than the height of the locking pin 27 which is situated on the inner side of the one bracket arm 19*a*, and which mates with a stop consisting of a pocket-drilled bore 28 when the surface 25 of the magazine 20 abuts the bracket arm 19*a* adjacent to said surface. The magazines 20 are able to slide backwards and forwards on their axle 23 in a generally circumferential direction relative to the axis of rotation, due to the play S between the two bracket arms 19*a* and 19*b* and the lateral surfaces of the magazines 20. Depending on the direction of rotation of the centrifuge shaft 14 or the shaft head 15, the magazines 20 either lie with their lateral surface 25 on the bracket arm 19*a* or, with the reversed direction of rotation, with their opposing lateral surface 26 on the bracket arm 19*b*** due to inertial forces acting on these magazines when the shaft is accelerated in either direction.

Figure 4:
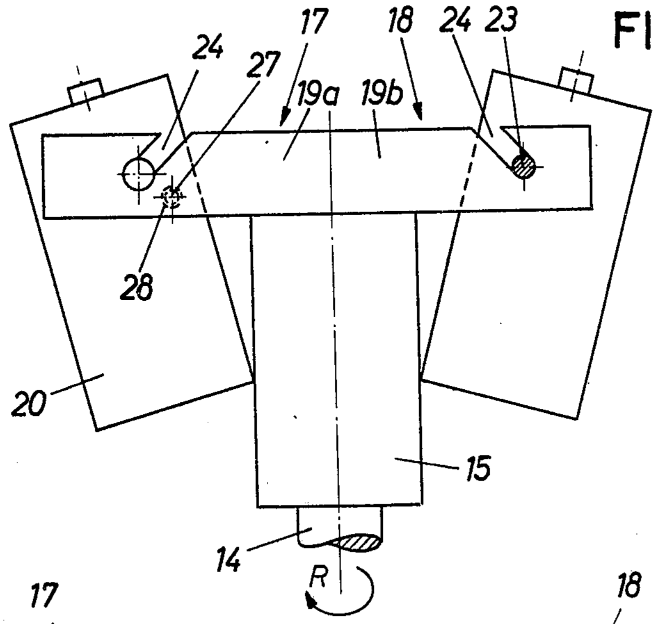
FIG. 4 shows a side elevation view of the shaft head during the removal of liquid from the sample containers.

The axles 23 run in bearing bores in the magazines 20, which lie eccentric to the axis through the center of the magazines 20, so that the magazines 20 have their lower end resting on the shaft head 15 in inoperative position (FIG. 4,5).

Figure 2:
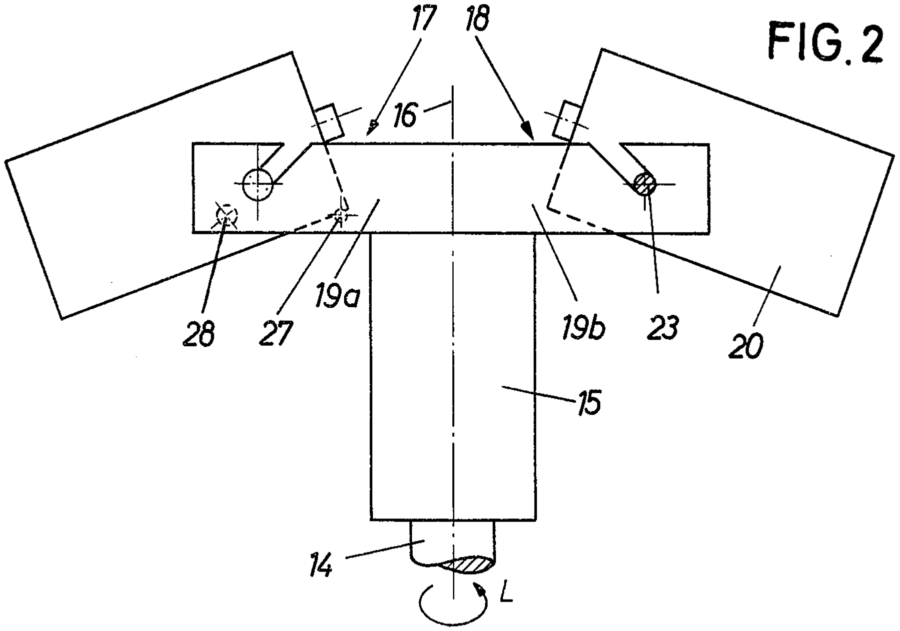
FIG. 2 shows a side elevation view of the shaft head situated inside the laboratory centrifuge housing, with the sample container-carrying magazines, during centrifugal action
Figure 3:
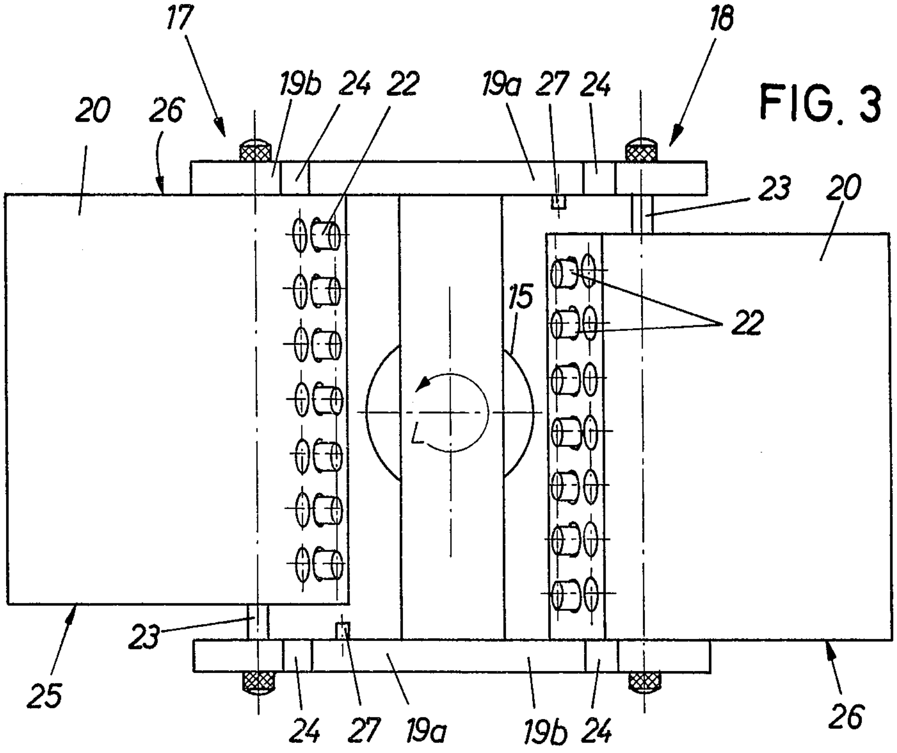
FIG. 3 shows a top plan view of the shaft head according to FIG. 2

For centrifuging, the centrifuge shaft 14 is driven in the one direction, i.e. counter clockwise ="L", whereupon the magazines 20 take up the position as shown in FIGS. 2 and 3. The magazines 20 then slide within the scope of the play S on their axle 23 against the bracket arms **19*b*, whereupon the stop bore 28 is released from the locking pin 27. Thus, with appropriate high rotational speed, the magazines 20** with their sample containers can swing their lower ends outwards to a centrifuge orientation so that substances suspended in the liquid can deposit on the bottom of the sample container.

Figure 5:
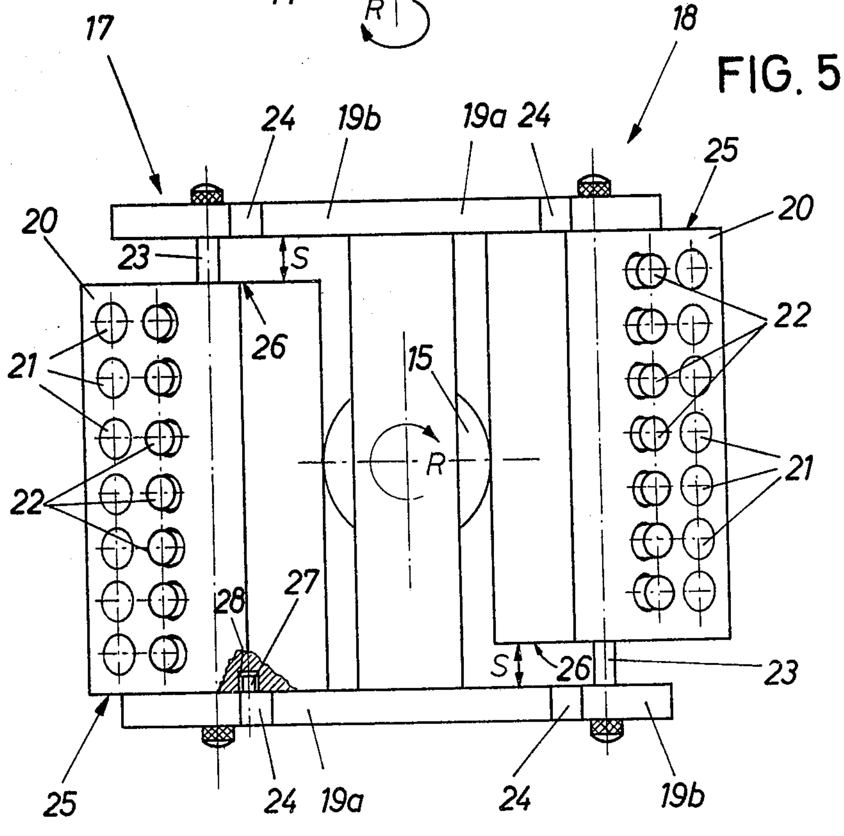
FIG. 5 shows a top plan view of the shaft head according to FIG. 4.

In order to subsequently remove the liquid situated in the sample containers from said containers while the substances deposited through the previous centrifugal action remain in the sample containers, the direction of rotation of the centrifuge shaft 14 is reversed after coming to a standstill. At the begining of this clockwise rotation =R, the magazines slide on their axle 23 against the bracket arms 19*a*, whereupon the locking pins 27 mate with the stop bores 28 and thus secure the magazines 20 in this inclined or slightly tilted decanting position caused by gravitation, as shown in FIGS. 4 and 5. In this position the magazines 20 as well as the sample containers 22 inserted in the magazines 20 have their top ends inclining outwards so that the liquid is flung out of the sample containers 22 at appropriately high rotational speed of the centrifuge shaft 14. Movement of a magazine along said axle may be described as generally circumferentially relative to the axis of rotation of said shaft and magazine, although said movement will obviously be in a straight line if said axle is straight.

With such a construction of the centrifuge head and the sample container-receiving magazine applicable to said head, merely the reversing of the direction of rotation is required in order to be able to perform the operating steps "centrifuging" and "liquid spin-off" successively without additional steps or agents. Changing the direction of rotation of the drive motor or centrifuge shaft is sufficient alone, whereupon the necessary switch operations take place automatically and the blocking of the magazines loaded with sample containers in the required position is achieved.

With the aforementioned embodiment, the axles 23 of the magazines are attached to the bracket arms 19*a*, 19*b* and the magazines can move on the axles 23. It is however also quite possible to firmly fix the magazines on the axles and to mount the axles in the bracket arms 19*a*, 19*b* with axial and rotational movement.

Bearing surfaces are expediently arranged between the axles 23 and the magazines 20 or the bracket arms 19*a*, 19*b*, said bearing surfaces having a coefficient of friction as low as possible so that the magazines can slide or run smoothly in axial and radial direction, thus ensuring that the switch-over from one operation phase to the other will function perfectly.

There are nozzles 31 present in the housing at predetermined points for the removal of liquids; with the present embodiment these are situated in the area of the rear wall of the housing 11 beneath the raised part of the cover 32. The liquid passes out through these nozzles upon actuation of the push switch 33 when the sample containers in the magazines are respectively situated beneath the nozzles 31. There is a control device situated beneath the control panel 13 on the front wall of the housing 11. This control device permits the running of predetermined operating programs without necessitating manual operation. The individual steps can of course also be controlled manually.

What is claimed is:

1. In a laboratory centrifuge for producing suspensions, carrying out washing processes and the like, the centrifuge including a shaft mounted in a housing for rotation about a generally vertical central axis and drivable selectively in either of two opposing directions, L and R, by a motor, said shaft including at its upper end a shaft head onto which magazines for receiving sample containers or similar objects are pivotally mounted, said shaft head including means whereby said magazines may be locked in a slightly tilted "decanting" orientation upon rotation in one direction and may be released to swing to a generally horizontal "centrifuge" orientation upon rotation in the other direction, the improvement characterized in that:

(a) said shaft head carrying the magazines is directly coupled to said shaft;

(b) at least one pair of brackets is located opposite each other, each bracket having a pair of arms projecting outwardly, the brackets arranged symmetrically to said central axis;

(c) each bracket arm further comprises an axle on which one of said magazines is eccentrically and pivotably mounted relative to a vertical centroidal axis therethrough, such that said magazine at rest hangs in said decanting orientation, and is swingable when rotated to said centrifuge orientation;

(d) each pair of bracket arms defines between them a distance in the horizontal direction greater than the width of said magazine in said direction by a distance, s, each magazine being drivable said distance, s, on said axle between a locked position abutting a first of said pair of bracket arms and a release position abutting said second of said pair of bracket arms;

and (e) locking means (i) automatically operable when said shaft is rotated in said direction R, and said magazine in decanting orientation is driven in direction L to said lock position, to lock said magazine in said decanting orientation, and (ii) automatically operable when said shaft is rotated in said direction L, to drive said magazine on said axle in direction R, to release position whereby, with continued shaft rotation in direction L, said magazine is then able to swing outward to said centrifuge orientation.

2. In a centrifuge device for centrifuging and subsequently decanting fluids in a sample container, said device including a housing, a shaft mounted on said housing for rotation about a central axis, the shaft having a head part, a motor for rotating said shaft selectively in either of opposite directions and at least one magazine for a sample container, the magazine being movably mounted on and rotatable with said head, said magazine also being pivotable from a slightly tilted "decanting" orientation to a "centrifuge" orientation extending generally radially outward, the improvement in combination therewith comprising mounting means for securing said magazine to said head while permitting said magazine to be movable thereon between said decanting and centrifuge orientations and further movable thereon between first and second positions spaced apart generally circumferentially relative to said central axis, said magazine being driven by inertial forces to said first or second positions when said shaft is rotated in said first or second direction respectively, said improvement further comprising locking means operable when said magazine is in said decanting orientation and is driven to said first position due to rotation of said shaft and magazine in said first direction, for automatically locking said magazine in decanting orientation, and for automatically unlocking said magazine from said decanting orientation by rotation of said shaft and magazine in said second direction, thereby driving said magazine from said first position to said second position where said magazine is then free to swing radially outward to said centrifuge orientation, said magazine also being swingable radially inward back to said decanting orientation when said rotation ceases.

3. A centrifuge device according to claim 2 wherein said mounting means comprises two arms spaced apart, axle means extending generally circumferentially between said arms, said magazine being pivotable on said axle means between said centrifuge and decanting orientations and movable lengthwise on said axle means between said first and second positions.

4. A centrifuge device according to claim 3 wherein said magazine when in said first position is adjacent said 1st arm, and said locking means comprises a first locking element on said first arm and a mating locking element on said magazine, said 1st and 2nd locking elements being locked together automatically when said magazine moves to said 1st position, and being automatically separated and unlocked when said magazine moves away from said 1st arm to said second position.

5. A centrifuge device according to claim 2 wherein said head and said shaft comprise a unitary member.

6. A centrifuge device according to claim 2 wherein said arms comprise components of a first bracket, said device comprises a pair of said brackets extending oppositely and arranged symmetrically about said axis.

7. A centrifuge device according to claim 2 said mounting means comprises means for suspending said magazine when at rest to hang in said decanting orientation.

8. A centrifuge device according to claim 2 comprising a pair of said magazines mounted similarly to said head and arranged symmetrically about said central axis.

9. A centrifuge device according to claim 8 wherein said mounting means for each of said magazines comprises a pair of arms extending radially outward and spaced apart generally circumferentially, means for suspending each of said magazines between said arms and permitting said magazine to swing between said decanting and centrifuge orientations and to move circumferentially between said arms between said 1st and 2nd positions.

10. A centrifuge device according to claim 4 wherein said 1st and 2nd locking elements comprise a pin extending generally circumferentially, and a mating bore respectively, said pin being extendible at least partially into said bore when said magazine moves to said locking position.

11. A centrifuge device according to claim 3 wherein each of said arms includes a slot opening in a generally upward direction and said rod has ends insertable downward into said slots.

* * * * *